United States Patent [19]

Villa et al.

[11] Patent Number: 5,084,569
[45] Date of Patent: Jan. 28, 1992

[54] TRIOXY BICYCLIC COMPOUNDS USEFUL FOR PREPARING OPTICALLY ACTIVE CARBOXYLIC ACIDS

[75] Inventors: Marco Villa, Milan; Claudio Giordano, Monza; Graziano Castaldi, Briona; Silvia Cavicchioli, Costermano, all of Italy

[73] Assignee: Zambon SPA, Vicenza, Italy

[21] Appl. No.: 493,752

[22] Filed: Mar. 15, 1990

Related U.S. Application Data

[62] Division of Ser. No. 137,000, Dec. 23, 1987, Pat. No. 4,922,009.

Foreign Application Priority Data

Dec. 23, 1986 [IT] Italy ................. 22822 A/86

[51] Int. Cl.⁵ ............................................. C07D 487/00
[52] U.S. Cl. ..................................... 544/148; 544/377; 546/207; 548/526; 549/274
[58] Field of Search ............ 549/274; 544/148, 378, 544/377; 546/207; 548/530, 526

[56] References Cited

U.S. PATENT DOCUMENTS

| | | | |
|---|---|---|---|
| 4,535,166 | 8/1985 | Castaldi | 562/496 |
| 4,542,237 | 9/1985 | Schloemer | 562/496 |
| 4,605,758 | 8/1986 | Schloemer | 562/496 |
| 4,620,031 | 10/1986 | Uggeri | 562/496 |
| 4,654,438 | 3/1987 | Schloemer | 562/496 |
| 4,670,586 | 6/1987 | Yube | 562/496 |

*Primary Examiner*—Michael L. Shippen
*Attorney, Agent, or Firm*—Cushman, Darby & Cushman

[57] ABSTRACT

A stereoconvergent process is described for preparing optically active alpha-arylalkanoic acids using as starting substance a diastereoisomeric mixture of ketals of formula

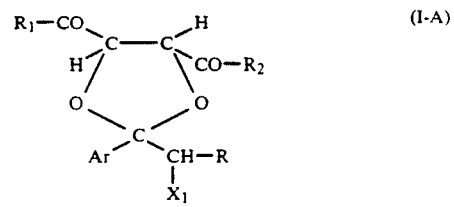

in which the substituents have the meanings given in the description.

The described process leads to the formation of a single enantiomer.

1 Claim, No Drawings

TRIOXY BICYCLIC COMPOUNDS USEFUL FOR PREPARING OPTICALLY ACTIVE CARBOXYLIC ACIDS

This is a division of application Ser. No. 07/137,000, filed Dec. 23, 1987, now U.S. Pat. No. 4,922,009.

This invention relates to a stereoconvergent process for preparing optically active carboxylic acids, and more particularly to a stereoconvergent process for preparing optically active alpha-arylalkanoic acids.

The terms associated with the stereochemical aspect of the processes discussed in the present context may be defined as follows:

"diastereoselective": a process which leads to the preferential formation of one of the possible diastereoisomers;

"enantioselective": as with a diastereoselective process an enantioselective process leads to the preferential formation of one of the enantiomers;

"stereoconvergent": a process which starting from diastereoisomer mixtures preferentially converts the various diastereoisomers into a single product in a sterically controlled manner.

European patent applications 158255 and 158913 (Zambon S.p.A.) describe alpha-functionalised alkyl-aryl-ketals of formula:

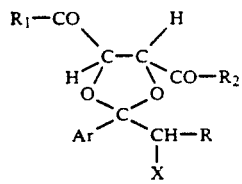

in which
Ar represents an aryl, possibly substituted;
R represents a linear or branched $C_1$-$C_4$ alkyl;
$R_1$ and $R_2$, which can be equal or different, represent a hydroxyl, an $O^-M^+$ group, $OR_3$ or $NR_4R_5$ in which $R_3$ represents a $C_1$-$C_{24}$ alkyl, a $C_3$-$C_6$ cycloalkyl, phenyl or benzyl; $M^+$ represents a cation of an alkaline metal, $R_4$ and $R_5$, which can be equal or different, represent a hydrogen atom, a $C_1$-$C_4$ alkyl, a $C_5$-$C_6$ cycloalkyl, a $(CH_2)_n$—$CH_2OH$ group where n=1, 2 or 3, or $R_4$ and $R_5$ together form a $(CH_2)_m$ group where M=4 or 5, a —$CH_2$—$CH_2$—$R_6$—$CH_2$—$CH_2$— group in which $R_6$ represents an oxygen atom, a NH group or a $C_1$-$C_4$ N-alkyl group;
X represents a chlorine, bromine or iodine atom, a hydroxyl, an alkoxy, alkylsulphonyloxy or arylsulphonyloxy group;
the carbon atoms marked with an asterisk both having either R or S configuration.

The compounds of formula I are prepared by a ketalisation reaction between a ketone of formula:

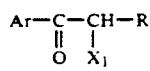

(in which Ar and R have the meanings given for formula I, and $X_1$ has the same meanings as X or represents a hydrogen atom) and L(+) or D(−)tartaric acid or their derivatives of formula:

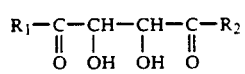

(in which $R_1$ and $R_2$ have the meanings given for formula I).

In this manner, the configuration of the two carbon atoms indicated by an asterisk (both R or both S) is predetermined according to the chosen derivative (III) of L(+) or D(−)tartaric acid respectively.

The two said centres of asymmetry are indicated hereinafter as a and b.

The compounds of formula I also have another asymmetric carbon atom, namely that to which the substituent X is bonded (this centre of asymmetry is indicated hereinafter as c).

The two aforesaid European patent applications describe the preparation of compounds of formula I as mixtures of two diastereoisomers which, with reference to the centres of asymmetry a, b and c in that order, can be indicated as (I, RRR)+(I, RRS) or alternatively (I, SSR)+(I, SSS).

The aforesaid documents also describe the preparation of diastereoisomeric mixtures strongly enriched with one of the two diastereoisomers and also the preparation of a single diastereoisomer.

The compounds of formula I, when subjected to a rearrangement reaction under different conditions according to the meaning of X, form alpha-arylalkanoic acids of formula:

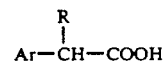

(in which Ar and R have the meanings given for formula I).

Rearranging ketals of formula I leads to alpha-arylalkanoic acids in which the enantiomeric excess mirrors the diastereoisomeric excess in the starting substance.

In addition, rearranging ketals of formula I in which X=Cl, Br or I in water at acid pH has proved enantioselective as it forms alpha-arylalkanoic acids in which the enantiomeric excess exceeds the diastereoisomeric excess in the starting substance.

The processes described in the said two European patent applications therefore enable the ketals of formula I to be prepared, if required, in a diastereoselective manner enriched with one of the two diastereoisomers, and allows subsequent rearrangement of said ketals enantioselectively, to obtain optically active alpha-arylalkanoic acids.

We have now surprisingly discovered that some of the ketals of formula I, and in particular those of formula I-A given below, are transformed by treatment under hot conditions with an aprotic dipolar solvent into new compounds of formula V in which the configuration of the centre of asymmetry c is inverted.

The compounds of formula I-A are as follows:

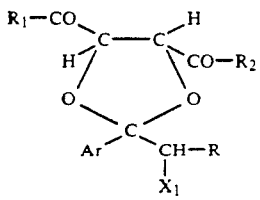

in which

Ar, R and $R_1$ have the meanings given for formula I;
$X_1$ represents a chlorine, bromine or iodine atom.

As stated heretofore, on treatment with a dipolar aprotic solvent under hot conditions, the compounds I-A are transformed into compounds of formula:

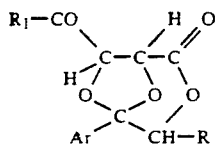

(in which Ar, R and $R_1$ have the aforesaid meanings).

In the transformation I-A→V we have observed that the centres of asymmetry a and b of the compounds I-A maintain the same configuration, whereas the carbon atom corresponding to the centre of asymmetry c in the compounds I-A inverts its configuration in the corresponding compounds V (this new centre of asymmetry is indicated hereinafter as c') as follows:

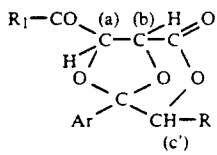

We have also discovered that by treating with a suitable solvent a mixture of two ketal diastereoisomers of formula I-A having the same configuration at the centres of asymmetry a and b, one of the two diastereoisomers is transformed into the corresponding compound V at a reaction rate much higher than that of the other, and this reaction is therefore diastereoselective.

Starting for example from a diastereoisomeric mixture of ketals of formula I-A having the configuration I-A (R,R,S) and I-A (R,R,R) in terms of the centres of asymmetry a, b and c, the compound of formula V having configuration V (R,R,S) in terms of the respective centres of asymmetry a, b and c is obtained with very high yield and very high diastereoselectivity, while at the same time the isomer I-A (R,R,S) remains unaltered.

These results can be summarised by the following equation:

I-A(R,R,S)+I-A(R,R,R)→I-A(R,R,S)+V(R,R,S)

A suitable solvent for transforming a ketal of formula I-A into the compound V is preferably a dipolar aprotic solvent or a similar system.

Examples of suitable solvents are dimethylformamide (DMF), dimethylacetamide (DMA), dimethylsulphoxide (DMSO), hexamethylphosphorotriamide (HMPA), N-methyl-pyrrolidone, polyglycol ethers, acetonitrile, benzonitrile, dioxane, tetrahydrofuran and diphenylether.

Systems equivalent to dipolar aprotic solvents signify systems consisting of a low polarity solvent in the presence of a phase transfer such as a quaternary ammonium salt or phosphonium, a crown ether or the like.

To implement said reaction it may be necessary, particularly if $R_1$ and/or $R_2$ are ester groups, to operate in the presence of a strong base chosen for example from alkaline metal hydroxides or hydrides.

Finally, we have discovered that hydrolysis of compounds of formula V leads to alpha-hydroxy-ketals of formula I in which X=OH with configuration retention.

The said alpha-hydroxyketals can be easily transformed into the corresponding alpha-alkyl or alpha-arylsulphonyloxyketals and these can be rearranged to alpha-arylalkanoic acids as described in the aforesaid European patent applications.

According to the present invention, by applying our aforesaid discovery in a suitable manner it is possible to implement a stereoconvergent process for preparing optically active alpha-arylalkanoic acids.

The process according to the present invention uses as its starting substance a mixture, in any diastereoisomeric ratio, of two diastereoisomer ketals of formula I-A having the same configuration at their centres of asymmetry a and b, and leads substantially to a single enantiomer of the corresponding alpha-arylalkanoic acid of formula IV.

In particular, starting from a diastereoisomeric mixture of ketals I-A with their centres of asymmetry a and b of R configuration, the corresponding alpha-arylalkanoic acid is obtained in the form of the single S enantiomer.

Likewise, starting from ketals I-A of S configuration at their centres a and b, the R enantiomer of the corresponding alpha-arylalkanoic acid is obtained.

The process of the present invention comprises:

A) treating a diastereoisomeric mixture or equivalent system of ketals of formula I-A with a dipolar aprotic solvent at a temperature between ambient and the boiling point of the reaction mixture, preferably between 80° and 100° C., possibly in the presence of a base to convert one of the two diastereoisomers into the corresponding compound of formula V with configuration inversion at the centre c;

B) rearranging the unreacted diastereoisomer I-A, preferably in water at acid pH, to obtain the corresponding alpha-arylalkanoic acid in the form of a single enantiomer;

C) hydrolysing the compound V to obtain the corresponding alpha-hydroxy-ketal with configuration retention;

D) rearranging the alpha-hydroxy-ketal, preferably after converting it into the corresponding arylsulphonyloxy or alkylsulphonyloxy derivative to obtain the corresponding alpha-arylalkanoic acid in the form of the same enantiomer as obtained in step B.

It is important to emphasise that if desired it is possible to implement the steps A, B, C and D without separating the products of any of the steps, so providing a process which, using a mixture of ketal diastereoisomers of any ratio, even in the ratio of 1:1, and without separating any intermediates, leads to a single enantiomer of the corresponding alpha-arylalkanoic acid.

The process of the invention can be schematised as follows, with reference to the preparation of alpha-arylalkanoic acids of formula IV in the form of the S enantiomer:

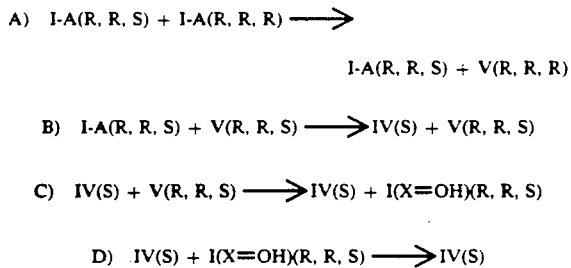

Scheme 1

A) I-A(R, R, S) + I-A(R, R, R) ⟶

I-A(R, R, S) + V(R, R, R)

B) I-A(R, R, S) + V(R, R, S) ⟶ IV(S) + V(R, R, S)

C) IV(S) + V(R, R, S) ⟶ IV(S) + I(X=OH)(R, R, S)

D) IV(S) + I(X=OH)(R, R, S) ⟶ IV(S)

Alternatively, if the products of step A are separated:

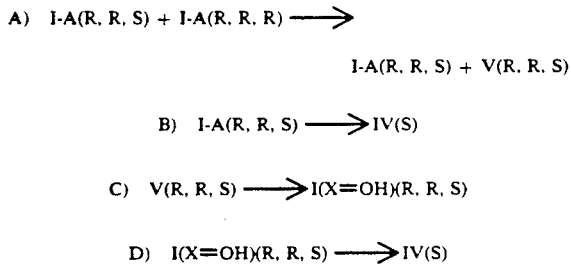

Scheme 2

A) I-A(R, R, S) + I-A(R, R, R) ⟶

I-A(R, R, S) + V(R, R, S)

B) I-A(R, R, S) ⟶ IV(S)

C) V(R, R, S) ⟶ I(X=OH)(R, R, S)

D) I(X=OH)(R, R, S) ⟶ IV(S)

It is also apparent that it is possible to separate the products of step B of Scheme 1 and proceed separately with the conversion of the compound V into the corresponding alpha-arylalkanoic acid.

The preparation of alpha-arylalkanoic acids of formula IV in the form of the R enantiomer is conducted in an analogous manner starting with a mixture of ketals I-A(S,S,S)+I-A(S,S,R).

As a further alternative, it is possible to conduct step C before step B.

In this case, the reaction scheme is as follows:

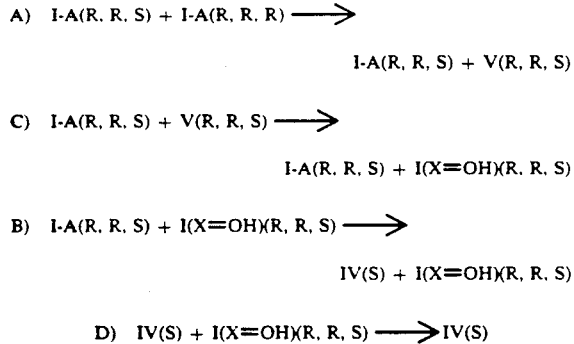

Scheme 3

A) I-A(R, R, S) + I-A(R, R, R) ⟶

I-A(R, R, S) + V(R, R, S)

C) I-A(R, R, S) + V(R, R, S) ⟶

I-A(R, R, S) + I(X=OH)(R, R, S)

B) I-A(R, R, S) + I(X=OH)(R, R, S) ⟶

IV(S) + I(X=OH)(R, R, S)

D) IV(S) + I(X=OH)(R, R, S) ⟶ IV(S)

Following Scheme 3, it is again possible to separate the two ketals obtained in step C and subject these to rearrangement separately in accordance with reactions B and D of Scheme 2.

A further alternative consists of separating the products of step B of Scheme 3 and separately rearranging the alpha-hydroxy-ketals in accordance with reaction D of Scheme 2.

Alpha-arylalkanoic acids of formula IV in the form of the R enantiomer are prepared in an analogous manner from a mixture of ketal diastereoisomers I-A(S,S,S) and I-A(S,S,R).

The operating conditions under which step A of the process is conducted have already been described.

Step B is conducted by the method already described in the aforesaid European patent applications, and preferably by treatment with water at acid pH as described in European patent application 158913.

We have observed that the said reaction can be conducted in the presence of the compound V without this influencing the reaction, while converting into the alpha-hydroxy-ketal having the same configuration at the centre c.

Step C of the process, i.e. hydrolysis of the compound V, can be conducted by conventional methods in an acid or basic environment.

The ketal I (X=OH) is converted into the corresponding alpha-arylalkanoic acid by transforming the compound into the corresponding alkylsulphonyloxy derivative (e.g. $X=O-SO_2-CH_3$) or arylsulphonyloxy derivative (e.g. $X=O-SO_2-C_6H_4-CH_3$) and rearranging this in a polar solvent. These reactions are described in European patent application 158255.

Alternatively, the alpha-hydroxy-ketals of formula I can be rearranged by treatment with $SO_2$ and chlorine, thionyl chloride, phosphorus trichloride, phosphorus tribromide, or phenoxysulphonylchloride in a dipolar aprotic solvent possibly in the presence of a base.

This process is described in the copending Italian patent application 21359 A/86 filed on 1 Aug. 1986 in the name of the present applicant.

According to a further aspect of the present invention, we have also discovered that ketals of formula I in which X is an alkylsulphonyloxy or arylsulphonyloxy group can be rearranged stereospecifically into the corresponding alpha-arylalkanoic acids by treatment with water at acid pH.

In addition, from a mixture of diastereoisomers of the said ketals alpha-arylalkanoic acids are obtained with greater optical purity than would be expected on the basis of the diastereoisomeric purity of the starting ketals.

For example, starting from a mixture of alpha-alkylsulphonyloxy or arylsulphonyloxy ketal c-centered epimers in the ratio of 90:10, the alpha-arylalkanoic acid of predominant configuration corresponding to the main diastereoisomer is obtained with 95% optical purity.

It is apparent to an expert of the art that the various process steps can also be used for other applications concerned with the synthesis of optically active alpha-arylalkanoic acids.

For example, step A of the process can be used as a method for separating ketal diastereoisomers of formula I-A.

The process of the present invention is therefore stereo-convergent in the sense that starting from a mixture of ketal diastereoisomers, substantially only one enantiomer of the corresponding alpha-arylalkanoic acid is obtained.

To our knowledge this is the first time a stereoconvergent process has been described for preparing optically active alpha-arylalkanoic acids.

Of these, S(+)-2-(6-methoxy-2-naphthyl)-propionic acid, an anti-inflammatory drug known as naproxen, is of particular importance.

One embodiment of our process involves stereoconvergent synthesis of naproxen.

This synthesis starts from ketal diastereoisomers of formula:

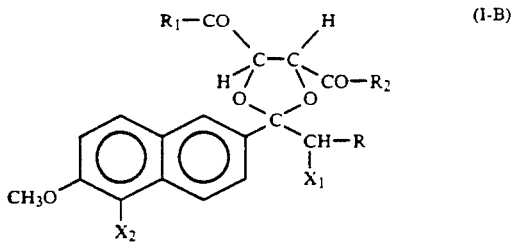

in which $R_1$, $R_2$ and $X_1$ have the meanings given for formula I-A and the substituent $X_2$ represents a hydrogen, chlorine, bromine or iodine atom, the centres of asymmetry a and b both have R configuration and the centre of asymmetry c can have any configuration.

The mixture of ketal diastereoisomers I-B is treated under hot conditions with a dipolar aprotic solvent to obtain conversion of the ketal I-B of R,R,R configuration into the compound of formula:

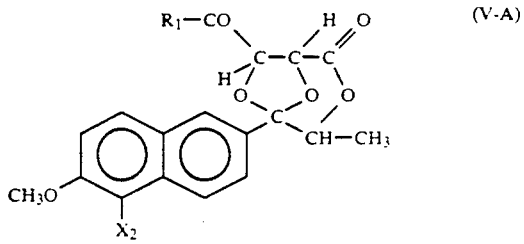

of R,R,S configuration.

The ketal diastereoisomer I-B (R,R,S) can be separated and rearranged as described heretofore to obtain naproxen in enantiomerically pure form, or one of its precursors if $X_2$ is other than hydrogen, from which naproxen is obtained by simple hydrogenolysis.

In contrast, the compound V-A is hydrolysed to obtain the alpha-hydroxy-ketal of formula:

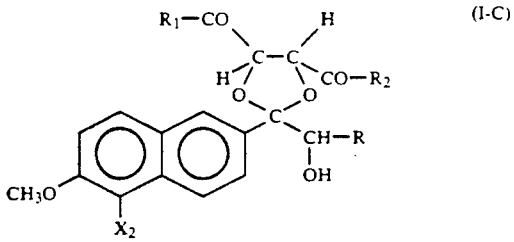

of R,R,S configuration.

This is then rearranged as stated heretofore to obtain naproxen (or its precursors if $X_2$ is other than hydrogen).

The yields and selectivities of the various steps are in all cases very high.

Thus starting from a diastereoisomeric mixture of ketals I-B, both the diastereoisomers can be transformed into the S(+) enantiomer of 2-(6-methoxy-2-naphthyl)-propionic acid.

According to a further aspect of the present invention, the compounds of formula V can be directly rearranged to alpha-arylalkanoic acids without passing through the corresponding alpha-hydroxy-ketals.

The compounds of formula V are rearranged in an inert solvent by treatment with protic acids or Lewis acids, to give optically active alpha-arylalkanoic acids.

The present invention therefore also relates to a process for preparing optically active alpha-arylalkanoic acids by rearranging a compound of formula V in the presence of protic or Lewis acids.

The following examples are given in order to better illustrate the invention.

EXAMPLE 1

Preparation of a mixture of diastereoisomers of 2-(1-bromoethyl)-2-(6-methoxy-2-naphthyl)-4(R),5(R)-dicarboxy-1,3-dioxolane in the ratio RRR:RRS=92:8 (Compound 1).

Trifluoromethanesulphonic acid (6.0 g; 4 mmoles) is added slowly to a solution of 2(R)-bromo-1-(6-methoxy-2-naphthyl)-propan-1-one (10 g; 34.1 mmoles), dimethyl tartrate (37.5 g; 211 mmoles) and dimethyl sulphite (13.8 g; 125 mmoles) in methylene chloride (10 ml) at 40° C. under magnetic stirring.

The solution is kept at 40° C. for 2 hours and then cooled, and poured into a 5% aqueous sodium carbonate solution (200 ml).

The aqueous solution is then extracted with ethyl ether (2×100 ml) and washed with water (50 ml).

The organic phase is dried over sodium sulphate, and the solvent evaporated under reduced pressure to give a residue (12.5 g). A 30% NaOH solution (10 ml) is dripped into a solution of this residue in toluene (10 ml).

After 3 hours, water (50 ml) and ethyl ether are added. The phases are separated and the organic phase is acidified to pH 1 with concentrated hydrochloric acid and extracted with ethyl ether (3×30 ml).

The organic phase is dried over sodium sulphate and the solvent evaporated under reduced pressure to give the compound (7.0 g; yield 48%) in a diastereoisomeric ratio of RRR:RRS=92:8.

EXAMPLE 2

Preparation of 2-[1(S)-hydroxyethyl]-2-(6-methoxy-2-naphthyl)-4(R),5(R)-dicarboxy-1,3-dioxolane and its methyl ester (Compound 2).

A mixture of the two diastereoisomers of the compound 1 (see Example 1) (1 g; 2.35 mmoles) is dissolved in an aqueous solution (50 ml) containing NaOH (0.16 g; 4 mmoles).

The solution, which has a pH of 5.4 at 22° C., is heated to 80° C. for 19 hours, the solution acidity being kept between pH 5.4 and pH 5.8 by adding a 0.2M NaOH solution.

The reaction mixture is then cooled to ambient temperature, raised to pH 12 with 2M NaOH and extracted with ethyl ether (10 ml).

The aqueous phase is then acidified with concentrated hydrochloric acid to pH 1 and extracted with ethyl ether (2×30 ml).

The organic phase is dried over sodium sulphate, and the solvent evaporated under reduced pressure to give a residue (0.9 g) consisting mainly of the required product.

The residue is esterified with diazomethane and subjected to silica gel chromatography (eluent: hexane/ethyl acetate 70:30) to give the compound 2.

$^1$H-NMR (CDCl$_3$—TMS) (300 MHz): delta (ppm): 1.10 (3H, s, J=6 Hz); 3.30 (3H, s); 3.89 (3H, s); 3.92 (3H, s); 4.15 (1H, q, J=6 Hz); 5.06 (2H, ABq, Δν=60.4, J=4.2 Hz); 7.35–8.19 (6H, m).

EXAMPLE 3

Preparation of the methylester of 1(R)-4-methyl-5-(6-methoxy-2-naphthyl)-3,6,8-trioxa-[3,2,1]-bicyclooctan-2-one-7(R)-carboxylic acid (Compound 3).

Sodium hydride (0.13 g; 5.4 mmoles) is added to a mixture of diastereoisomers of compound 1 (see Example 1) (2 g; 4.7 mmoles) in DMF (40 ml) kept stirring at 22° C. under an inert atmosphere.

The solution is then heated to 87° C. for 15 hours. On termination of the reaction, the solvent is evaporated under reduced pressure and the residue dissolved in water (50 ml).

The aqueous solution is acidified to pH 1 with concentrated hydrochloric acid and extracted with ethyl ether (2×30 ml).

The pooled organic phases are dried over sodium sulphate and evaporated under reduced pressure.

A residue is obtained which after evaporating to dryness and treating with diazomethane is subjected to silica gel chromatography (eluent: hexane/ethyl acetate 8:2) to obtain the compound 3 (0.99 g; yield 59%).

IR (KBr) 1780 cm$^{-1}$ (C=0) $^1$H-NMR (CDCl$_3$–TMS) (300 MHz): delta (ppm): 1.14 (3H, d, J=6.6 Hz); 3.66 (3H, s); 3.93 (3H, s); 4.90 (1H, q, J=6.6 Hz); 4.95 (1H, s); 5.31 (1H, s); 7.15–8 (6H, m).

EXAMPLE 4

Preparation of compound 2 (see Example 2) by hydrolysis of compound 3 (see Example 3).

A solution of NaOH (0.24 g; 6 mmoles) in water (2 ml) is added to a solution of the compound 3 (see Example 3) (0.99 g; 2.77 mmoles) in methylene chloride (2 ml).

After 2 hours the solution is diluted with water (30 ml), acidified to pH 1 with concentrated hydrochloric acid and extracted with ethyl ether (2×30 ml).

The pooled organic phases are dried over sodium sulphate and evaporated under reduced pressure.

A residue is obtained which is esterified with diazomethane to give the compound 2 which is then purified by crystallisation from MeOH (1.00 g; 2.16 mmoles; yield 95%).

EXAMPLE 5

Preparation of 2-[1(S)-methanesulphonyloxyethyl]-2-(6-methoxy-2-naphthyl)-4(R),5(R)-dimethoxycarbonyl-1,3-dioxolane (Compound 5).

Methanesulphonylchloride (0.31 g; 2.7 mmoles) is added slowly to a solution of the compound 2 (1.00 g; 2.6 mmoles) in methylene chloride (10 ml) at 0° C. and triethylamine (0.27 g; 2.7 mmoles).

The reaction mixture is left at 22° C. for 2 hours and then poured into a aqueous 8% sodium bicarbonate solution (20 ml) and methylene chloride (20 ml).

The separated organic phase is dried over sodium sulphate and evaporated under reduced pressure.

Crystallisation from methanol gives the required product (1.02 g; 2.18 mmoles; yield 84%).

$^1$H-NMR (CDCl$_3$–TMS) (90 MHz): delta (ppm): 1.38 (3H, d, J=6 Hz); 2.93 (3H, s); 3.37 (3H, s); 3.86 (3H, s); 3.90 (3H, s); 4.80 (1H, q, J=6 Hz); 5.03 (2H, ABq, Δν=5.09, J=4.2 Hz); 7.06–8.00 (6H, m).

EXAMPLE 6

Preparation of the methyl ester of 2(S)-(6-methoxy-2-naphthyl)propionic acid.

A solution of compound 5 (see Example 3) (1 g; 2.13 mmoles), methanol (7.5 ml) and water (2.5 ml) is heated to 150° C. for 5 hours in a closed tube.

The reaction mixture is then cooled to 22° C., diluted with water (20 ml) and extracted with ethyl ether (2×10 ml).

The pooled organic phases are dried over sodium sulphate and evaporated. The residue is purified by silica gel chromatography (eluent: dichloromethane) to give the required compound (0.42 g; 1.64 mmoles; yield 77%).

Analysis (300 MHz) conducted in CDCl$_3$ using an optically active shift reagent (tris-[3-(heptafluoropropyl-hydroxymethylene)-d-camphorate], Europium (III) derivative) shows an enantiomer excess exceeding 98%.

EXAMPLE 7

Preparation of pure 2-[1(S)-bromoethyl]-2-(6-methoxy-2-naphthyl)-4(R),5(R)-dimethoxycarbonyl-1,3-dioxolane.

Sodium hydride (2.4 g; 100 mmoles) is added to a mixture of 2-(1-bromoethyl)-2-(6-methoxy-2-naphthyl)-4(R),5(R)-carboxy-1,3-dioxolane (38.1 g; 90 mmoles; diastereoisomer ratio RRS:RRR=89:11) in dimethylformamide (300 ml) at 22° C. under an inert atmosphere.

When gas ceases to evolve the solution is heated to 87° C. for 48 hours. The solvent is then evaporated under reduced pressure and the residue is taken up in water (300 ml).

The aqueous solution is acidified to pH 1 with concentrated hydrochloric acid and extracted with ethyl ether (3×100 ml).

The pooled organic phases are dried over sodium sulphate and evaporated to dryness to give a residue, which is dissolved in methanol (400 ml) and concentrated sulphuric acid (0.6 ml).

After 3 hours heating under reflux, the solution is cooled and sodium carbonate (2.0 g; 20 mmoles) added.

On evaporating the solvent an impure product is obtained which is dissolved in acetone (100 ml), filtered and evaporated to dryness.

The residue obtained in this manner is purified by silica gel chromatography (eluent: hexane/ethyl acetate=75:25).

The required pure product is thus obtained (28.5 g; 63 mmoles; yield 78% calculated on the initial RRS diastereoisomer).

EXAMPLE 8

A solution of bromine (1.34 g, 8.4 mmol) in carbon tetrachloride (3 ml) was added, dropwise at 0° C. under nitrogen, to a solution of 2-(1-bromoethyl)-2-(6-methoxy-2-naphthyl)-1,3-dioxolane-4(R), 5(R)-dicarboxylic acid dimethyl ester (diastereomeric ratio RRR:RRS=92:8, 95 g, 8.2 mmol). The reaction was kept at 0° C. for 1 h, poured into a 10% aqueous solution of sodium carbonate. The organic layer was separated, washed with water, and dried over sodium sulfate. Evaporation of the solvent in vacuo gave a diastereomeric mixture of 2-(1-bromoethyl)-2-(5-bromo-6-methoxy-2-naphthyl)-1,3-dioxolane-4(R), 5(R)-dicarboxylic acid in a ratio RRR:RRS=90:10.

The product was dissolved in toluene and the solution was added at ambient temperature with an aqueous solution of sodium hydroxyde. The reaction mixture was kept at ambient temperature for 3 hours and worked up as described in example 1 to give a diasteromeric mixture of 2-(1-bromoethyl)-2-(5-bromo-6-methoxy-2-naphthyl)-1,3-dioxolane-4(R), 5(R)-dicarboxylic acid in a ratio RRR:RRS=90:10.

EXAMPLE 9

Preparation of 1(R)-4(S)-methyl-5-(5-bromo-6-methoxy-2-naphthyl)-3,6,8-triossan-[3,2,1]-bicyclooctan-2-one-7(R)-carboxylic acid compound 6.

Carrying out the reaction as described in example 3 starting from the diasteromeric mixture of 2-(1-bromoethyl-2-(5-bromo-6-methoxy-2-naphthyl)-1,3-dioxolane-4(R), 5(R)-dicarboxylic acid (ratio RRR:RRS=90:10, 3,2 g, 6.09 mmol) compound 6 was obtained in 70% yield.

EXAMPLE 10

Preparation of 1(R)-4-(S)-methyl-5-(5-bromo-6-methoxy-2-naphthyl)-3,6,8-trioxan-[3,2,1]-bicyclooctan-2-one-7(R)-carboxylic acid methyl ester: compound 7.

Compound 7 was obtained, after purification on column chromatography, by reacting compound 6 with diazomethane. IR in $CH_2Cl_2$(1%) 1760 cm$^{-1}$ (stretching C-O). $^1$H-NMR (300 MHz) (CDCl$_3$) δ ppm 1.13 (d, 3H, J=6.6 Hz); 4.05 (s, 3H); 4.90 (q, 1h, J=6.6 Hz); 4.93 (s, 1H); 5.31 (s, 1H); 7.33-8.33 (m, 5H, aromatic protons).

EXAMPLE 11

Carrying on the experiment as described on example 4 starting from compound 7 the 2-(1-(S)-hydroxyethyl)-1,3-dioxolane-4(R), 5(R)-dicarboxylic acid dimethyl ester (compound 8) was obtained in 90% yield.

EXAMPLE 12

Starting from compound 8 and carrying out the experiment as described in example 5 the 2-(1-(S)-methanesulfonyloxy-ethyl)-1,3-dioxolane-4(R), 5(R)-dicarboxylic acid dimethyl ester (compound 9) was obtained in 80% yield.

EXAMPLE 13

Starting from compound 9 and carrying out the experiment as described in example 6 the enantiomerically pure 2-(5-bromo-6-methoxy-2-naphthyl)-propanoic acid methyl ester was obtained as shown by $^1$H-NMR analysis carried out in the presence of europium III tris-(3-heptafluoropropylhydroxymethylene-d-camphorate).

We claim:

1. A compound of formula

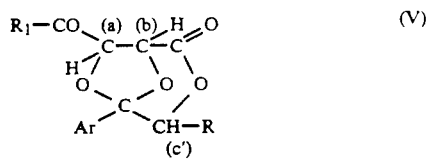

in which Ar represents a group of the formula

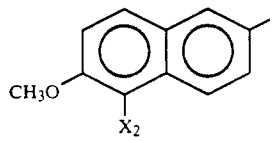

in which $X_2$ represents a hydrogen, chlorine, bromine or iodine atom; and R represents a linear or branched $C_1-C_4$ alkyl; and $R_1$ represents a hydroxyl, an O—M$^+$ group, OR$_3$ or NR$_4$R$_5$ in which R$_3$ represents a $C_1-C_{24}$ alkyl, a $C_3-C_6$ cycloalkyl, phenyl or benzyl; M$^+$ represents a cation of an alkaline metal, R$_4$ and R$_5$, which can be equal or different, represent a hydrogen atom, a $C_1-C_4$ alkyl, a $C_5-C_6$ cycloalkyl, a $<CH_2>_n$—CH$_2$OH group where n=1, 2 or 3, or R$_4$ and R$_5$ together form a $<CH_2>_m$ group where m=4 or 5, a —CH$_2$—CH$_2$—R$_6$—CH$_2$—CH$_2$— group in which R$_6$ represents an oxygen atom, a NH group or a $C_1-C_4$ N-alkyl group; and the ring carbon atoms marked with an (a) or (b) both having either R or S configuration, and the other carbon atom marked with a (c') having any configuration.

* * * * *